United States Patent [19]

Long

[11] Patent Number: 5,167,922
[45] Date of Patent: Dec. 1, 1992

[54] ASSAY CARTRIDGE

[75] Inventor: Ernest W. Long, Concord, Mass.

[73] Assignee: PB Diagnostic Systems Inc., Westwood, Mass.

[21] Appl. No.: 515,242

[22] Filed: Apr. 27, 1990

[51] Int. Cl.⁵ .......................................... G01N 31/22
[52] U.S. Cl. ...................................... 422/58; 422/64; 422/102; 436/47
[58] Field of Search ................ 422/61, 102, 64, 58; 435/45, 47, 165; 356/244, 246; 220/346, 347; 206/560, 562

[56] References Cited

U.S. PATENT DOCUMENTS

| | | | |
|---|---|---|---|
| 3,884,641 | 5/1975 | Keaffczyk et al. | 422/58 |
| 4,090,789 | 5/1978 | Macemon et al. | 356/85 |
| 4,387,992 | 6/1983 | Swartz | 356/246 |
| 4,454,095 | 6/1984 | Holt | 422/64 |
| 4,457,894 | 7/1984 | Clark et al. | 422/73 |
| 4,517,851 | 5/1985 | Tice | 73/864.91 |
| 4,584,275 | 4/1986 | Okano et al. | 435/290 |
| 4,623,519 | 11/1986 | Cornut et al. | 422/72 |
| 4,898,195 | 2/1990 | Sussman | 220/347 |
| 5,035,861 | 7/1991 | Grondone | 422/64 |
| 5,053,197 | 10/1991 | Bowen | 422/58 |
| 5,075,077 | 12/1991 | Durley, III et al. | 422/58 X |

Primary Examiner—Jill A. Johnston
Attorney, Agent, or Firm—Gaetano D. Maccarone

[57] ABSTRACT

An assay cartridge suitable for use with automated analytical instruments which include a conveyor such as a carousel. The cartridge is configured with ledges extending outwardly from sides thereof, preferably at the bottom of the cartridge. The conveyor incudes berths for receiving the cartridges, each berth being formed as a depressed region within a top surface of the conveyor and bounded by a floor at the bottom of the berth and opposed sidewalls and an end wall extending upwardly from the floor. The sidewalls are preferably parallel to each other. An open end of the berth, opposite the end wall serves as a port through which the cartridge is inserted and extracted from the berth. Each of the sidewalls of the berth is provided with a shoulder which extends inwardly towards a center line of the berth, and upon insertion of the cartridge, extends over the ledges of the cartridge to serve as a guide. The guide includes grooves formed between the shoulders and the floor. Cantilevered tongues are formed in the cartridge ledges, on opposite sides of the cartridge, for interaction with the grooves, regions of the floor being recessed beneath the shoulders to form depression for reception of the cantilevered tongues. The tongues are configured for interaction with the shoulders to force the tongues into the depressions for locking the cartridge into the berth. Ends of the depression are inclined to facilitate a lifting of the tongues out of the depression upon extraction of the cartridge from the berth.

5 Claims, 3 Drawing Sheets

ASSAY CARTRIDGE

BACKGROUND OF THE INVENTION

This invention relates to assay cartridges suitable for use in automated analytical systems employing a conveyor for transport of such cartridges among various work stations and, more particularly, to a cartridge which is provided with a spring catch for securing the cartridge in a nest on the conveyor.

Various types of chemical tests can be performed by automated test equipment, an example of testing of considerable interest being the assay of biological substances for human health care. Automated test equipment allows large numbers of test samples to be processed rapidly. Such equipment is employed in health care institutions including hospitals and laboratories. Biological fluids, such as whole blood, plasma or serum are tested to find evidence of disease, to monitor therapeutic drug levels, etc.

In the automated test instrument a sample of the test fluid is typically provided in a sample cup and all of the process steps including pipetting of the sample onto an assay test element, incubation and readout of the signal obtained are carried out automatically. The test instrument typically includes a series of work stations each of which performs a specific step in the test procedure. The assay element or cartridge is typically transported from one work station to the next by means of a conveyor such as a carousel to enable the test steps to be accomplished sequentially. The conveyor usually carries a plurality of the assay cartridges, each secured to a specific location on the upper surface of the conveyor. In the usual arrangement, the assay cartridges are spaced apart from each other in berths which are located along the periphery of the conveyor to facilitate automatic insertion and extraction.

It is necessary to construct the berths for the assay cartridges in a fashion which permits the cartridge to be inserted readily without any binding along the walls of the berth. Such binding or any other such impediment would interfere with precise placement of the cartridge within its berth. Similarly, upon extraction of the cartridge, there should be no binding or other impediment which might interfere with the operation of the automated analytical instrument. Consequently, it has been the practice to construct the berths with smooth interior surfaces which allow the cartridges to be slid readily into and out of the berths.

Another important consideration is the need to ensure that the assay cartridges are precisely positioned on the conveyor and further, that they are not displaced from their positions during movement of the conveyor. The precise positioning of the assay cartridges is necessary for proper operation of the instrument. For example, the fluid dispensing assembly typically includes a pipette which obtains sample fluid from a sample cup and is then transported to the assay cartridge to dispense the required volume of sample fluid. Any excessive misalignment of the pipette with assay cartridge could result in spillage or an incorrect volume being deposited on the assay element thereby causing inaccurate test results.

As a result of the aforementioned smooth-walled berths and correspondingly smooth-walled assay cartridges, the latter may not be held as securely in their respective positions as would be desirable. Accordingly, it is an object of this invention to provide an assay cartridge which can be securely held in its required location on a conveyor while at the same time being readily inserted into and removed from such location.

SUMMARY OF THE INVENTION

These and other objects and advantages are accomplished in accordance with the invention by providing an assay cartridge comprising a housing which includes a circumferential sidewall, a top wall and at least one aperture to permit fluids to be provided to a reaction zone within the cartridge. The housing may be molded as a unitary structure from a suitable polymeric material which may be clear or opaque and may include a colorant. The polymeric material is inert to the fluids utilized in the test procedure. The cartridge also may include a base member which is adapted to be inserted inside the bottom periphery of the housing.

A perimetric portion of each side of the sidewall extends therefrom to form a ledge. The berths of the conveyor into which the assay cartridge are to be inserted are constructed each with opposed sidewalls connected by an end wall, the sidewalls and the end wall upstanding from a floor of the berth. An opening opposite the end wall serves as an entry port by which a cartridge is inserted into the berth. A portion of each sidewall, away from the floor, protrudes in the manner of a shoulder to form a groove between the shoulder and the floor of the berth. The groove receives the ledge of a cartridge. This permits a cartridge to be inserted into a berth with the cartridge ledge captured by the berth groove. The sidewall shoulders of the berth contact both sides of the cartridge, and the end wall of the berth contacts a front end of the cartridge to accurately position the cartridge with respect to a plane, normally a horizontal plane, of the conveyor. The groove and the ledge interact to accurately position the cartridge on the conveyor.

In accordance with a further feature of the invention, the cartridge is retained within its berth by means of a spring catch molded integrally with the ledge of the cartridge. The catch is formed by a tongue on each side of the cartridge, the tongue being a part of the ledge and extending in a longitudinal direction of the cartridge. A portion of the material of the ledge, in the shape of an elongated curved slit, is deleted from the ledge to define each tongue. A spring force of the tongue produces pressure between opposed top and bottom surfaces of the groove as the tongue enters the groove upon insertion of the cartridge into the berth. A portion of the floor of the berth is recessed to form a depression at the site of the groove to relieve the pressure of the tongue and, thereby, form a mild snap action by which the spring action of the tongue tends to retain the cartridge against longitudinal movement within the berth. While the snap-action force of the tongue is sufficient to retain the cartridge in its position during motion of the carousel, the snap-action force is readily overcome by an eject mechanism for ejection of the cartridge from its berth at the completion of a test procedure.

BRIEF DESCRIPTION OF THE DRAWINGS

The aforementioned aspects and other features of the invention are explained in the following description, taken in connection with the accompanying drawings wherein.

DESCRIPTION OF THE PREFERRED EMBODIMENTS

Figure 1:
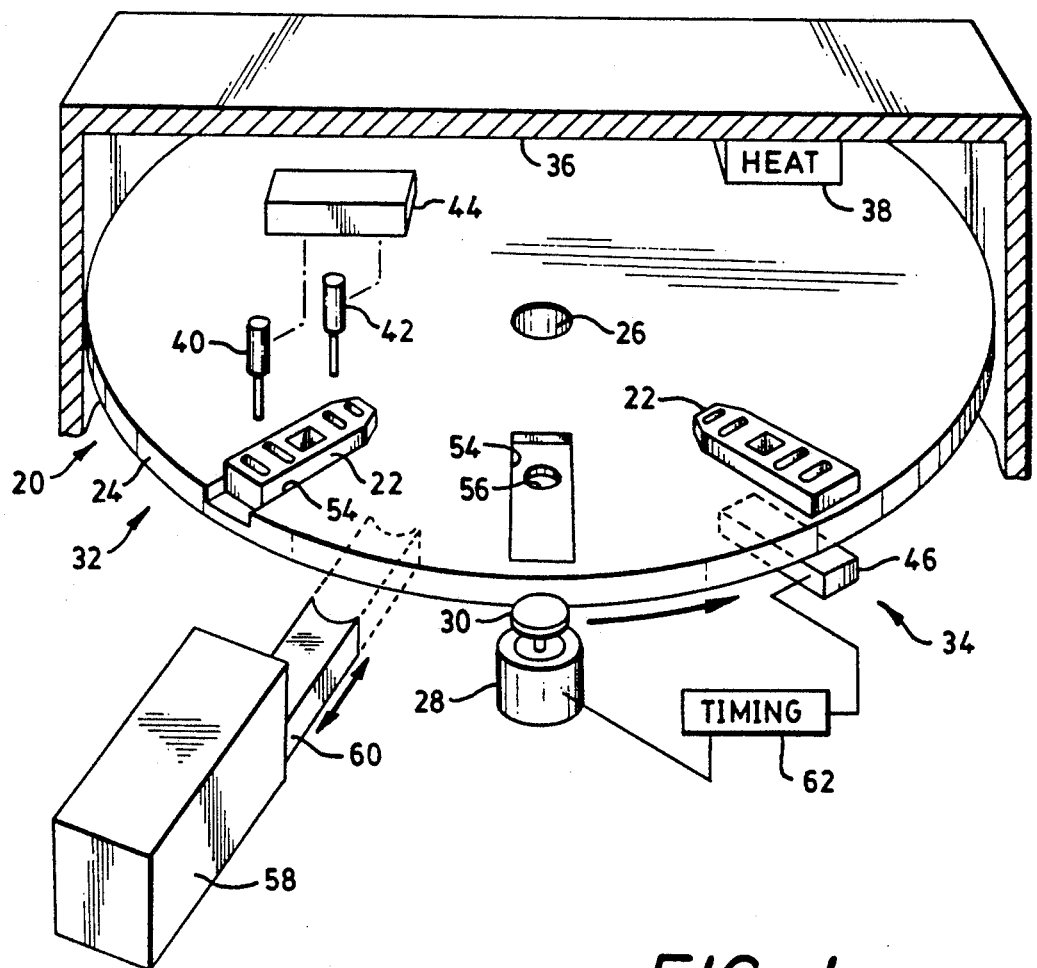
FIG. 1 is a stylized view, partially diagrammatic, of a test system employing cartridges of the invention, the system employing a preferred embodiment of a conveyor, i.e., a carousel for moving the cartridges among various work stations.

In FIG. 1 there is shown an analytical instrument 20 which provides automatically a sequence of process steps to accomplish an assay of a test sample. A plurality of cartridges 22 are employed within the instrument 20 to increase the throughput rate, one process step being carried out with one cartridge concurrently with the performance of other process steps with other cartridges. The cartridges 22 are illustrated with respect to a preferred embodiment thereof which includes one or more chambers in the housing. Such chambers may be configured as wells, or reservoirs, for the storage and/or mixing of fluids which are used in the assay procedure or the chambers may culminate in an opening to permit fluids to be provided to a reaction zone within the cartridge. The chambers are formed, integrally within the housing of the cartridge.

The analytical instrument 20 includes a turntable or carousel 24 which is rotated about an axle 26 by a motor 28. By way of example, the motor 28 may be mechanically coupled to the carousel 24 by a gear 30. The carousel 24 carries the cartridges 22 from one work station to another work station, two such work stations 32 and 34 being shown, by way of example, in FIG. 1. The carousel 24 rotates within a temperature controlled chamber 36 having a heater 38 for maintaining a desired temperature at the various work stations so as to allow for a process step of incubation.

Work station 32 is a pipetting station whereat sample fluid and any other required test reagents are delivered to the assay cartridges 22. By way of example, there are shown two pipettes 40 and 42. Preferably, the pipettes are utilized with disposable pipette tips (not shown), each disposable tip being used for delivery of one fluid only and then discarded so as to avoid contamination which could lead to errors in the assay result. The pipettes 40 and 42 are positioned and operated by a pipette mechanism 44 mechanically connected to the pipettes 40 and 42, as indicated by dashed lines.

During the assay procedure, as a result of the reaction(s) and/or interaction(s) between the sample fluid and the test reagent(s) which take place, a detectable change is effected corresponding to the presence of an analyte or component of interest in the sample fluid. The detectable change may be a color change which may be read spectrophotometrically such as with a densitometer or, in an assay method based on fluorescent-labeled biologically active species or one which involves the generation of a fluorescent species as a result of a reaction between test reagents, a fluorescent output signal can be generated and read spectrofluorometrically. Such detectable changes may be read from above or below the assay cartridge. At work station 34 there is shown by way of example a fluorometer 46 for irradiating the reaction zone within the assay cartridge and for measuring the fluorescence emitted from the fluorescent species present therein.

The carousel 24 may be arranged so as to accomodate varying numbers of assay cartridges 22. Each position, or berth, 54 for holding an assay cartridge is provided in this embodiment with a small aperture 56 to allow the irradiating illumination to reach the reaction zone in the assay cartridge and to permit the reflected fluorescent emissions to be collected and measured. Also shown is an injector 58 for inserting a cartridge 22 in an empty berth 54, the injector 58 having an arm 60 for gripping a cartridge 22 during the insertion operation. The injector 58 also serves to extract a cartridge from a berth 54 by use of the arm 60 upon completion of a test procedure. Operation of the motor 28, the pipette mechanism 44, the fluorometer 46 and the injector 58 are synchronized by means of a timing unit 62.

Figure 2:
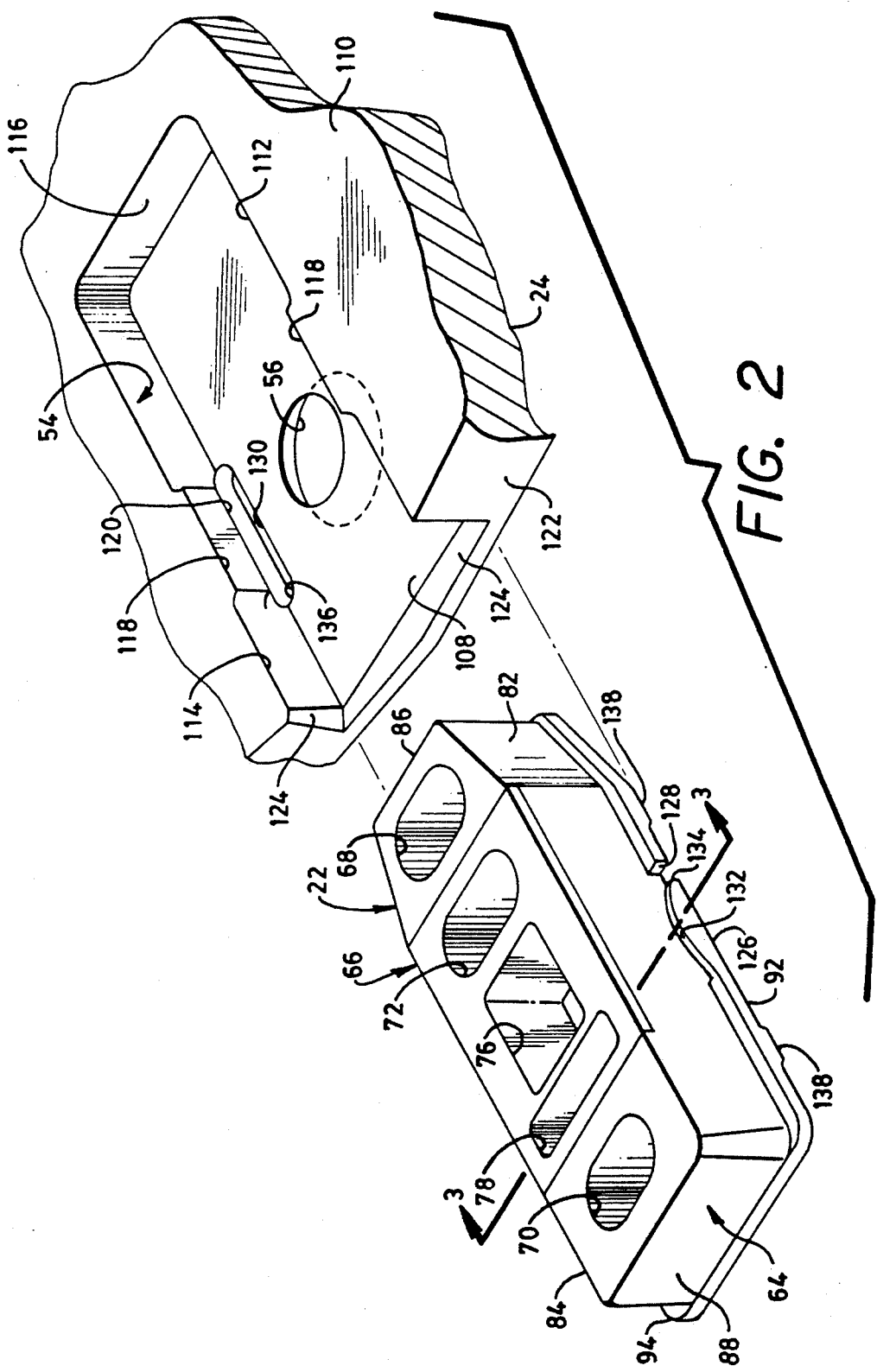
FIG. 2 is a fragmentary view of the carousel of FIG. 1, the view including a berth for reception of a cartridge shown also in FIG. 2.
Figure 3:
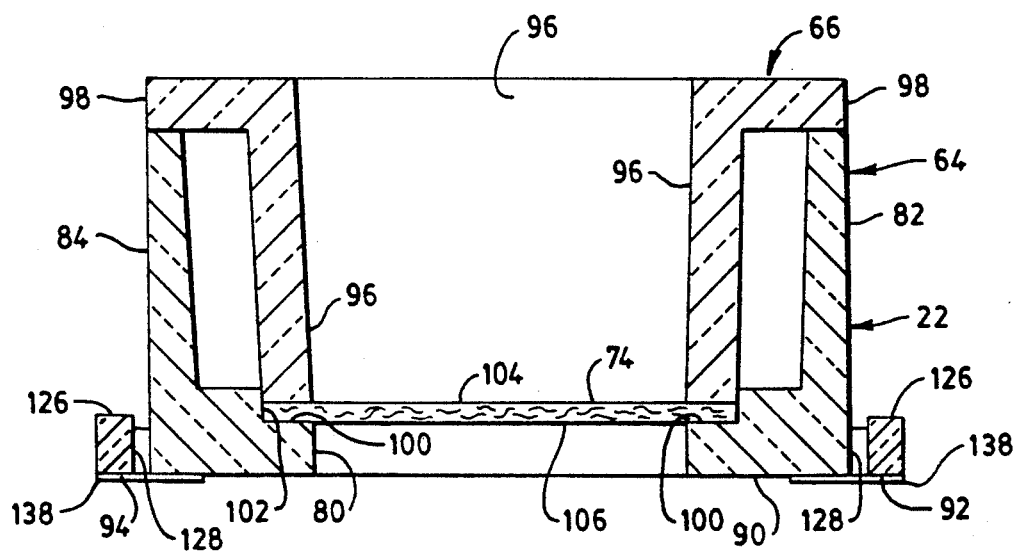
FIG. 3 is a sectional view of the cartridge, taken along the line 3—3 in FIG. 2.

As noted previously, the assay cartridge of the invention may be provided in various configurations and may include one or more chambers such as reservoirs for holding test reagents or for mixing test reagents, or such as wells for permitting fluid reagents to be provided to a reaction zone within the cartridge. FIGS. 2 and 3 show details of the construction of a preferred assay cartridge 22 and the insertion of the assay cartridge into a berth 54 on the carousel 24.

The assay cartridge 22 is contructed of a housing 64, the housing 64 including an insert 66 to facilitate construction of the cartridge 22. A front reservoir 68 and a back reservoir 70 are formed within the housing 64 for containing fluid reagents. A mixing bowl 72 is formed within the insert 66 for mixing reagents, which reagents may be obtained from either of the reservoirs 68 and 70 as well as from reagents delivered by the pipettes 42 and 44 from an external reservoir (not shown). Reagents can be applied to the reaction zone of the assay cartridge through access port 76 formed within insert 66. Dispenser 78 can also be used to provide fluid reagents to the reaction zone. Bottom window 80 is provided for irradiating the reaction zone with readout illumination.

The housing 64 has the general shape of a boat and includes sidewalls 82 and 84 which are joined together by a front wall 86 and a back wall 88, the four walls 82, 84, 86 and 88 upstanding from a base plate 90. The four walls 82, 84, 86, 88, and the plate 90 are molded from plastic as a unitary structure. A first ledge 92 extends horizontally from the plate 90 and from the bottom of the sidewall 82, and a second ledge 94 extends horizontally from the plate 90 and from the bottom of the sidewall 84.

The insert 66 comprises a set of walls 96 which extend in a generally vertical direction downwardly from a top flange 98 of the insert 66, the top flange extending horizontally from the wall 96 to contact and to rest upon the sidewalls 82 and 84. The four walls 96 define the port 76. The bottom window 80 is formed within the base plate 90. At the sides of the bottom window 80, as shown in FIG. 3, the plate 90 is formed with shoulders 100 into which walls 96 depend, bottom edges of the walls 96 coacting with the shoulders 100 to form a guide 102 for locating a fibrous pad 74 in the bottom of the cartridge 22. Bottom edges of the walls 96 contact a top surface 104 of the pad 74, while the shoulders 100 contact a bottom surface 106 of the pad 74. The central portion of the fibrous pad serves as the reaction zone in the assay cartridge shown.

The berth 54 comprises a floor 108 which is depressed from the top surface 110 of the carousel 24. The floor 108 is surrounded by sidewalls 112 and 114 and an end wall 116 which extend from the floor 108 to the carousel surface 110. The end of the berth 54 opposite the end wall 116 is open to serve as a port for insertion of a cartridge into the berth 54. The aperture 56 is located within the floor 108. Shoulders 118 extend from each of the sidewalls 112 and 114 in a direction generally parallel to the floor 108 to form grooves 120 between the shoulders 118 and the floor 108. The locations of the shoulders 118 are retracted from the ends of the sidewalls 112 and 114 towards a more central location of the sidewalls 112 and 114. An outer circular surface 122 of the carousel 24 is provided with a chamber 124 at the site of the berth 54, the chamber 124 extending along an interfacing edge of the surface 122 with the floor 108 and each of the sidewalls 112 and 114 of the berth 54. The chamber 124 facilitates alignment of the cartridge 22 with a berth 54 during insertion of the cartridge 22 into the berth 54 by the injector 58 (FIG. 1).

In accordance with the invention, the ledges 92 and 94 slide within the grooves 120 upon insertion of the cartridge 22 in the berth 54. Opposite sides of the grooves 120, constituted by the floor 108 and the underside of each of the shoulders 118, are spaced apart by a distance equal to a thickness of the ledges 92 and 94 plus a slight clearance space to facilitate entry of the ledges 92 and 94 within the corresponding grooves 120 so as to secure the cartridge 22 within the berth 54 with respect to a vertical direction perpendicular to a top surface 110 of the carousel 24. The shoulders 118 are spaced apart from each other with a distance equal to the width of the cartridge 22 plus a slight clearance for accurately locating the cartridge 22 in the berth 54 with respect to a horizontal direction parallel to the top surface 110 of the carousel 24.

In accordance with a feature of the invention, each of the ledges 92 and 94 is provided with a cantilevered tongue 126 formed within the process of forming the housing 64 by deleting material of each of the ledges 92 and 94 in the form of an elongated slit 128. In each of the ledges 92 and 94, the end of the tongue 126 closest to the rear of the cartridge 22 is attached to the ledge 92, 94 while the opposite end of the tongue 126 is free to be displaced in the vertical direction against a restoring spring force of the tongue 126. At each of the grooves 120, a depression 130 is formed within the floor 108 of the berth 54 to facilitate reception of the tongue 126 upon insertion of the cartridge 22 within the berth 54. A central portion 132 of the tongue 126 is enlarged in the vertical direction for contacting the shoulder 118, during insertion of the cartridge 22 within the berth 54, and for bending the tongue 126 downward into the depression 130 as the back end 134 of the tongue 126 clears the back end 136 of the depression 130. This may be likened to a snap action in which the back end 134 of the tongue 126 is displaced in the vertical direction alongside the back end 136 of the depression 130 to lock the cartridge 22 within the berth 54, and hold the cartridge 22 with its front wall 86 in abutment to the end wall 116 of the berth 54. It is noted that while only the groove 120 of the sidewall 114, and only the tongue 126 of the ledge 92 are shown in FIG. 2, the foregoing description applies equally to the tongues 126 in both of the ledges 92 and 94 and to both of the depressions 130 alongside the sidewalls 112 and 114. As an additional constructional feature, pods 138 may be provided in forward and aft portions of the cartridge 22 under each of the ledges 92 and 94 to facilitate the sliding movement of the cartridge 22 along the floor 108 of the berth 54. The back end 136 of the depression 150 is angled relative to the plane of the floor 108 to facilitate a lifting of the back end 154 of the plane 126 out of the depression 130 upon extraction of the cartridge 22 from the berth 54.

The foregoing construction provides for an accurate positioning of the cartridge 24 within the berth 54 in three dimensions, namely, the vertical direction perpendicular to the top surface 110 of the carousel 24, and two horizontal directions parallel to the surface 110, namely, the tangential and the radial directions of the carousel 24. The sidewalls 112 and 114 with their shoulders 118 act as a guide for positioning the cartridge 22 in the tangential direction, the grooves 120 serve as a guide for positioning the cartridge 22 in the vertical direction, and the locking of the back ends 134 of the tongues 126 in the back ends 136 of the depressions 130 serve with the abutment of the front of the cartridge 22 against the end wall 116 as a guide for positioning the cartridge 22 in the radial direction. Accordingly, the assay cartridges are held precisely and firmly in the desired locations and are not displaced to any significant extent when the carousel is rotated quickly to carry a particular assay cartridge to a work station in order that a method step may be performed.

The assay cartridges of the invention may include test reagents for performing any of various analytical test methods including those based on chemical reactions, immunometric interactions, etc. Although these assay cartridges are preferably utilized for the analysis of biological fluids such as plasma, serum, etc., it will be evident to those skilled in the art that the cartridges may be used to carry out analyses of any fluid. In a preferred embodiment the assay cartridges are used to carry out immunometric assays for an analyte of interest, e.g., an antigen or an antibody. Such assays, as well as the other types which can be carried out with the assay cartridges of the invention are well known to those skilled in the art and extensive discussion thereof is not required here. By way of illustration the use of the assay cartridge shown in FIGS. 1-3 will be described in conjunction with a sandwich immunoassay for an antigen of interest. In assay cartridge 22, the thin porous member 74, which may be a fibrous mesh pad, a porous membrane or the like serves as the location where the immunometric interactions take place. In this preferred embodiment the porous member 74 extends from the dispenser 78 to a chamber (not shown) in the front of the housing 64 which holds a fluid absorbing material (not shown). In this assay an antibody raised against the antigen of interest is initially applied to the porous member 74 and immobilized therein prior to the pad being incorporated into the assay cartridge 22. Applicaton of the antibodies to the porous member and immobilization of the antibodies therein can be accomplished by any of various known techniques. For example, a fluid containing the antibodies can be applied to the porous member and the member subsequently dried to provide a porous member having the antibodies distributed throughout and held therein by the structure of the member. In other embodiments, particularly where the porous member comprises a fibrous mesh material, antibodies can be chemically bound to polymeric particles and the fibrous mesh impregnated with an immunocomplex of the antibodies. In this manner the antibodies are immobilized in the fibrous paid and remain therein throughout the assay process.

In the assay process a volume of sample fluid, typically 20-30 $\mu$l, is aspirated into a pipette from a sample cup and deposited on the porous member 74 through access port 76 while the assay cartridge 22 resides on the carousel 24. The sample fluid is drawn throughout the porous member via capillary action and the assay cartridge is allowed to incubate for a suitable period at the appropriate temperature to allow the sample antigen to interact with the immobilized antibodies dispersed throughout the member. Subsequently, a foil cover (not shown) which is secured about the mouth of reservoir 68 to form a seal over a solution of an enzyme-linked antibody (an antibody directed to the same antigen as is the antibody immobilized in the porous member), is perforated by means of a pipette, 40 or 42, carrying a disposable tip and a desired volume of the enzyme-linked antibody solution, typically 10–20 μl, is aspirated into the pipette tip. The solution is then deposited onto porous member 74 through access port 76 and drawn throughout the member by capillary action. The assay cartridge 22 is again allowed to incubate to permit the interactions between the enzyme-linked antibodies and the sample antigen to occur thus forming the ternary complex with the immobilized antibodies and the sample antigens. Since the enzyme label must be detected indirectly, a desired volume, typically 50–100 μl, of a solution of a substrate for the enzyme is applied to the porous member. This is accomplished by piercing the foil covering (not shown) of reservoir 70 with a disposable pipette tip carried by pipette 40 or 42 and aspirating the desired volume into the pipette tip. This substrate solution is utilized both as a wash fluid to remove from the porous member any unbound sample antigen and enzyme-linked antibodies and to render the enzyme label detectable. The substrate solution is deposited into the dispenser 78. The substrate solution exits the dispenser and is guided into the porous member 74. As the substrate solution propagates through the porous member 74 it forces any unbound sample antigen and enzyme-linked antibody together with the fluid out of the porous member and into the absorber chamber where they are taken up by absorber material. The duration of this step is approximately 1–2 minutes. The signal provided by the fluorescent species liberated by the reaction of the enzyme with the substrate material is read by means of the fluorometer 46.

It will, of course, be evident that the assay process described above can be modified by utilizing a separate wash fluid such as water to replace the fluid in the porous member and guide area and to remove unbound antigens and enzyme-linked antibodies. In this procedure the substrate solution is applied to the porous member after the wash fluid.

In another preferred embodiment a thin multilayer assay element is incorporated in the assay cartridge. Such multilayer assay elements for use in automated analytical instruments are well known to those skilled in the art.

Although the invention has been described with respect to a specific preferred embodiment it is evident that this is illustrative only and other embodiments of the invention will be apparent to those skilled in the art.

What is claimed is:

1. An assay cartridge which is adapted to be operative in an analytical instrument which includes an assay cartridge carrier having a berth for receiving the cartridge and a guide structure for releasably securing the cartridge to the carrier, the cartridge comprising:
   a housing which includes opposed sidewalls and a ledge extending longitudinally from each said sidewall;
   tongue means being formed as a part of each of said ledges and being cantilevered from said ledges, said tongue means being configured for mating with the guide structure of an assay cartridge carrier for releasably securing the cartridge to the carrier;
   assay means in said housing for receiving a sample fluid and for providing a detectable signal in response to the presence of a component of interest in said fluid; and
   an aperture in said housing to permit a fluid to be provided to said assay means.

2. A cartridge according to claim 1 wherein said ledges are located at the bottom of said sidewalls of said cartridge.

3. A cartridge according to claim 1 wherein said tongue means at each of said ledges is formed as a tongue having an enlarged central portion.

4. A cartridge according to claim 1 wherein said sidewalls extend in a vertical direction between top and bottom surfaces of the cartridge, and said tongue means can flex in said vertical direction.

5. A cartridge according to claim 1 wherein said housing further includes at least one well for storage of test reagents and/or for mixing test reagents.

* * * * *